(12) United States Patent
Eyckerman et al.

(10) Patent No.: US 8,048,986 B2
(45) Date of Patent: Nov. 1, 2011

(54) REVERSED MAMMALIAN PROTEIN-PROTEIN INTERACTION TRAP

(75) Inventors: Sven Eyckerman, Nazareth (BE); Jan Tavernier, Balegem (BE); Joel S. Vandekerckhove, Loppem (BE)

(73) Assignee: Vlaams Interuniversitair Instituut Voor Biotechnologie VZW, Gent (BE)

( * ) Notice: Subject to any disclaimer, the term of this patent is extended or adjusted under 35 U.S.C. 154(b) by 0 days.

(21) Appl. No.: 12/653,513

(22) Filed: Dec. 14, 2009

(65) Prior Publication Data

US 2010/0174049 A1    Jul. 8, 2010

Related U.S. Application Data

(60) Division of application No. 10/751,072, filed on Jan. 2, 2004, now abandoned, which is a continuation of application No. PCT/EP02/07419, filed on Jul. 2, 2002.

(30) Foreign Application Priority Data

Jul. 3, 2001 (EP) .................................. 01202569

(51) Int. Cl.
*C07K 14/715* (2006.01)
*C07K 19/00* (2006.01)
*G01N 33/567* (2006.01)
*C07H 21/04* (2006.01)

(52) U.S. Cl. ...................... 530/350; 435/7.21; 536/23.5
(58) Field of Classification Search .......................... None
See application file for complete search history.

(56) References Cited

U.S. PATENT DOCUMENTS

| | | | |
|---|---|---|---|
| 5,525,490 A | 6/1996 | Erickson et al. |
| 5,637,463 A | 6/1997 | Dalton et al. |
| 5,733,726 A | 3/1998 | Fu et al. |
| 5,885,779 A | 3/1999 | Sadowski et al. |
| 5,935,797 A | 8/1999 | Clayberger et al. |
| 6,303,319 B1 | 10/2001 | Rickles |
| 6,479,280 B1 | 11/2002 | Muyldermans et al. |
| 2002/0019006 A1 | 2/2002 | Yuan et al. |

FOREIGN PATENT DOCUMENTS

| | | |
|---|---|---|
| EP | 1 088 892 A1 | 4/2001 |
| FR | 2 782 084 A1 | 2/2000 |
| WO | WO 90/02809 | 3/1990 |
| WO | WO 92/20791 | 11/1992 |
| WO | WO 95/26400 | 10/1995 |
| WO | WO 97/10330 | 3/1997 |
| WO | WO 97/31113 | 8/1997 |

(Continued)

OTHER PUBLICATIONS

Bannasch et al., Oncogene, 1999, pp. 6810-6817, vol. 18.

(Continued)

*Primary Examiner* — Robert Landsman
*Assistant Examiner* — Zachary Howard
(74) *Attorney, Agent, or Firm* — TraskBritt

(57) ABSTRACT

The invention relates to a recombinant receptor, comprising a ligand-binding domain and a signaling domain that comprises a heterologous bait polypeptide, which receptor is inactivated by binding of a prey polypeptide to the heterologous bait peptide, either in presence or absence of a ligand binding to the ligand-binding domain. The receptor is activated by addition of a compound that disrupts the bait-prey interaction. The invention also relates to a method of screening compounds that disrupt compound-compound binding using the recombinant receptor.

14 Claims, 6 Drawing Sheets

FOREIGN PATENT DOCUMENTS

| | | |
|---|---|---|
| WO | WO 97/32017 | 9/1997 |
| WO | WO 98/13502 | 4/1998 |
| WO | WO 99/66324 | 12/1999 |
| WO | WO 00/07014 | 2/2000 |
| WO | WO 00/08148 | 2/2000 |
| WO | WO 00/46406 | 8/2000 |
| WO | WO 01/90188 A2 | 11/2001 |
| WO | WO 03/004643 A2 | 1/2003 |

OTHER PUBLICATIONS

Bao et al., Oncogene, 1996, pp. 2171-2176, vol. 12.

Estojak et al., Molecular and Cellular Biology, 1995, pp. 5820-5829, vol. 15, No. 10.

European Office Action for application 02 767 173.4 dated Oct. 16, 2007.

European Office Action for application 02 767 173.4 dated Jul. 27, 2009.

European Office Action for application 02 767 173.4 dated Oct. 20, 2005.

Expressions: A newsletter for gene cloning and expression, Invitrogen, 1999, pp. 1-16.

Eyckerman et al., Eur Cytokine Netw, 1999, pp. 549-556, vol. 10, No. 4.

Eyckerman et al., Identification of the Y985 and Y1077 motifs as SOCS3 recruitment sites in the murine leptin receptor, FEBS Letters, 2000, pp. 33-37, vol. 486.

Eyckerman et al., Nature Methods, 2005, pp. 427-433, vol. 2, No. 6.

Fashena et al., The continued evolution of two-hybrid screening approaches in yeast: how to outwit different preys with different baits, Gene, 2000, pp. 1-14, vol. 250.

Fujiwara et al., Biochemistry, 2000, pp. 12729-12738, vol. 41, No. 42.

GenBank Accession NM_14616, 6 pages, printed Jan. 16, 2008.

Haan et al., Biochemical Pharmacology, 2006, pp. 1538-1546, vol. 72.

Hertveldt et al., Identification of Gal80p-interacting proteins by *Saccharomyces cerevisiae* whole genome phage display, Gene, 2003, pp. 141-149, vol. 307.

Hilpert et al., Protein Engineering, 2001, pp. 803-806 (11 pages as printed), vol. 14, No. 10.

Ihle et al., Trends Genet, 1995, pp. 69-74, vol. 11, No. 2.

Junqueira et al., Oncogene, 2003, pp. 2772-2781, vol. 22.

Li et al., Leptin receptor activation of SH2 domain containing protein tyrosine phosphatase 2 modulates Ob receptor signal transduction, Proc. Natl. Acad. Sci., Aug. 1999, pp. 9677-9682, vol. 96, USA.

Massotte et al., Abstract, Parameters influencing human mu opioid receptor over-expression in baculovirus-infected insect cells, J. of Biotechnology, 1999, pp. 39-45, vol. 69.

Medici et al., The EMBO Journal, 1997, pp. 7241-7249, vol. 16, No. 24.

Muthukumaran et al., Journal of Biological Chemistry, 1997, pp. 4993-4999, vol. 272, No. 8.

Nicholson et al., PNAS, published Jun. 6, 2000, pp. 6493-6498, vol. 97, No. 12.

Osborne et al., The Yeast Tribrid System—Genetic Detection of trans-phosphorylated ITAM-SH2-Interactions, Bio/technology, Dec. 1995, pp. 1474-1478, vol. 13.

Overton et al., Current Biology, 2000, pp. 341-344, vol. 10, No. 6.

PCT International Preliminary Examination Report, PCT/EP02/07419, dated Feb. 10, 2004.

PCT International Search Report, PCT/EP02/07419, dated Dec. 20, 2002.

Van Criekinge et al., Yeast Two-Hybrid: State of the Art, Biological Procedures Online, Oct. 4, 1999, vol. 2, No. 1 <www.biologicalprocedures.com>.

Zhang et al., Nature Biotechnology, 2000, pp. 71-74, vol. 18.

Office Action for U.S. Appl. No. 10/751,072 dated Feb. 8, 2005.

Office Action for U.S. Appl. No. 10/751,072 dated Jul. 29, 2005.

Office Action for U.S. Appl. No. 10/751,072 dated Jan. 24, 2006.

Office Action for U.S. Appl. No. 10/751,072 dated Oct. 10, 2006.

Office Action for U.S. Appl. No. 10/751,072 dated Apr. 5, 2007.

Office Action for U.S. Appl. No. 10/751,072 dated Jan. 2, 2008.

Office Action for U.S. Appl. No. 10/751,072 dated Apr. 22, 2008.

Office Action for U.S. Appl. No. 10/751,072 dated Nov. 10, 2008.

Office Action for U.S. Appl. No. 10/751,072 dated Mar. 9, 2009.

Office Action for U.S. Appl. No. 10/751,072 dated Oct. 13, 2009.

U.S. Appl. No. 10/303,157, filed Nov. 22, 2002, Eyckerman et al., Receptor-Based Interaction Trap.

U.S. Appl. No. 10/751,072, filed Jan. 2, 2004, Eyckerman et al., Reversed Mammalian Protein-Protein Interaction Trap.

U.S. Appl. No. 12/459,278, filed Jun. 29, 2009, Kas et al., Peptide Combos and Their Uses.

U.S. Appl. No. 11/305,737, filed Dec. 16, 2005, Kas et al., Peptide Combos and Their Uses.

REVERSED MAMMALIAN PROTEIN-PROTEIN INTERACTION TRAP

CROSS-REFERENCE TO RELATED APPLICATION

This patent application is a continuation of co-pending U.S. patent application Ser. No. 10/751,072, filed Jan. 2, 2004, wherein each application is a continuation of PCT International Patent Application No. PCT/EP02/07419, filed on Jul. 2, 2002, designating the United States of America, and published, in English, as PCT International Publication No. WO 03/004643 A2 on Jan. 16, 2003, which PCT application (and this application) claim priority to EP 01202569.8 filed Jul. 3, 2001, the entire contents of each of which are hereby incorporated herein by this reference.

TECHNICAL FIELD

The invention relates generally to biotechnology, and more particularly to a recombinant receptor comprising a ligand-binding domain and a signaling domain that comprises a heterologous bait polypeptide, which receptor is inactivated by binding of a prey polypeptide to the heterologous bait peptide, either in presence or absence of a ligand binding to the ligand-binding domain. The receptor is activated by addition of a compound that disrupts the bait-prey interaction. The invention also relates to a method of screening compounds that disrupt compound-compound binding using the recombinant receptor.

BACKGROUND

Protein-protein interactions are an essential key in biological processes, from the replication and expression of genes to the morphogenesis of organisms. Protein-protein interactions govern, amongst other things, ligand-receptor interaction and the subsequent signaling pathway; they are important in assembly of enzyme subunits, in the formation of biological supramolecular structures such as ribosomes, filaments, and virus particles and in antigen-antibody interactions.

Researchers have developed several approaches in attempts to identify protein-protein interactions. Co-purification of proteins and co-immunoprecipitation were amongst the first techniques used. However, these methods are tedious and do not allow high throughput screening. A major breakthrough was obtained by the introduction of the genetic approaches, of which the yeast two-hybrid (Fields and Song, 1989) is the most important one. Several improvements and modifications of this system have been published. As an example, we can cite U.S. Pat. No. 5,637,463 that describes a method of detecting post-translational modification-dependent protein-protein interactions.

Approaches based on phage display do avoid the nuclear translocation. PCT International Publication No. WO 90/02809 describes how a binding protein can be displayed on the surface of a genetic package, such as a filamentous phage, whereby the gene encoding the binding protein is packaged inside the phage. Phages, which bear the binding protein that recognizes the target molecule, are isolated and amplified. Several improvements of the phage display approach have been proposed, as described, for example, in PCT International Publication Nos. WO 92/20791, WO 97/10330, and WO 97/32017.

Another technique for assessing protein-protein interactions is based on fluorescence resonance energy transfer (FRET) or bioluminescence resonance energy transfer (BRET) (PCT International Publication No. WO 99/66324).

Although in principle, all of those methods can be used in a positive (detecting protein-protein interactions) or a negative (detection of disruption of the protein-protein interaction) way, due to the positive selection in case of protein-protein interaction, none of these methods is really suited for screening of compounds that inhibit protein-protein interaction. To overcome this problem, U.S. Pat. No. 5,733,726 discloses a cytotoxicity-based genetic selection method, whereby a classic two-hybrid system is linked to the transcriptional activation of a toxic reporter gene, providing an assay for positive selection of mutations or small molecules or drugs disruptive for protein-protein interaction. An adaptation of this method has been disclosed in PCT International Publication No. WO 98/13502, whereby the protein-protein interaction induces the transcription of a repressor gene, which represses a selectable marker. Upon disruption of the protein-protein interaction, the repressor will no longer be synthesized, resulting in an activation of the selectable marker.

DISCLOSURE OF INVENTION

Surprisingly, it has been found that the signaling pathway of a receptor can be inhibited by recruitment of an inhibitor to the receptor using a bait-prey interaction. The signaling pathway can be restored by addition of a compound that disrupts the bait-prey interaction. As the bait-prey interaction has to be very efficient to obtain a sufficient inhibition of the signaling, the system is very sensitive and even a weak disruption of the bait-prey interaction can be detected, contrary to systems with a toxic reporter gene, as described above, where complete inhibition of the interaction may be needed to allow survival of the cells.

Therefore, provided are methods of screening compounds that disrupt compound-compound interaction which satisfies this need and provides additional advantages as well. The principle of the method is illustrated in FIG. 1.

It is one aspect of the invention to provide a recombinant transmembrane receptor, comprising an extracellular ligand-binding domain and a cytoplasmic domain that comprises a heterologous bait polypeptide, whereby the activation of the receptor is inhibited by binding of a prey polypeptide to the heterologous bait peptide. In one preferred embodiment, the heterologous prey polypeptide comprises an inhibitor of the activation site of the receptor. Preferably, the inhibitor may directly inhibit the modifying enzyme activity that is activating the activation site of the receptor, or it may bind to the activation site and block the modification of the site, or it may remove the modification from the activation site, or it may change the conformation of either the modifying enzyme or the activation site, making a modification impossible. In another preferred embodiment, the heterologous prey polypeptide comprises an inhibitor of the signaling pathway of the receptor. Preferably, the inhibitor of the signaling pathway binds to a signaling pathway molecule and prevents it from binding to the activation site, or it inhibits its modification after binding to the activation site. In still another preferred embodiment, the heterologous prey polypeptide comprises a recruitment site for an inhibitor of the activation of the receptor or for an inhibitor of the signaling pathway of the receptor, as defined above.

Preferably, the recombinant receptor is a chimeric receptor in which the ligand-binding domain and the cytoplasmic domain are derived from two different receptors. Even more preferably, the receptor is a multimerizing receptor. This can be a homomultimerizing receptor as well as a heteromultimerizing receptor. The cytoplasmic domain of the recombinant receptor comprises a heterologous bait polypeptide which can be fused to the carboxyterminal end, or can replace a part of this carboxyterminal end, or can be situated in the cytoplasmic domain itself as an insertion or a replacement of an endogenous internal fragment. In case of a heteromultimerizing receptor, not all the chains need to comprise the bait, but it is sufficient if one of the composing chains does comprise the bait in its cytoplasmic domain. Insertion of the heterologous bait polypeptide may result in one or more deletions of the original cytoplasmic domain. The only limiting factor for the modifications in the cytoplasmic domain is that the cytoplasmic domain should retain, directly or indirectly, its inherent modifying enzyme activity, either by retaining a modifying enzyme activity-binding site such as a Jak-binding site or by incorporating an active modifying enzyme activity in the cytoplasmic domain itself, and that the cytoplasmic domain should retain, directly or indirectly, at least one activation site. This activation site is not necessarily situated on the cytoplasmic domain itself, but may be situated on another polypeptide that binds, directly or indirectly, to the cytoplasmic domain. Activation of the receptor and of the signaling pathway is achieved by binding of a ligand to the ligand-binding domain of the receptor and by disruption of the binding of a prey polypeptide to the heterologous bait polypeptide comprised in the cytoplasmic domain of the receptor. Alternatively, a constitutively activated (i.e., non-ligand-dependent) receptor may be used, whereby the activation is inhibited by binding of a prey polypeptide to the heterologous bait polypeptide comprised in the cytoplasmic domain of the receptor, which then may solely be activated by disruption of the binding.

One embodiment is a recombinant transmembrane receptor according to the invention whereby the activation site is a phosphorylation site and the modifying enzyme activity is a kinase.

Another embodiment of the invention is a homomultimerizing recombinant leptin receptor, with a heterologous bait polypeptide fused into or, preferentially, at the carboxyterminal end of its cytoplasmic domain. The heterologous bait polypeptide may replace part of the cytoplasmic domain as long as the Jak-binding site and at least one activation site are retained.

The invention also provide a recombinant receptor comprising an extracellular ligand-binding domain and a cytoplasmic domain that comprises a heterologous bait polypeptide which can be modified by modifications such as, but not limited to, phosphorylation, acetylation, acylation, methylation, ubiquitinilation, glycosylation or proteolytic processing, whereby the recombinant receptor is activated by binding of a ligand to the ligand-binding domain and by disruption of the binding of a prey polypeptide to the heterologous bait polypeptide and whereby the binding of the prey polypeptide to the heterologous bait polypeptide is dependent upon the modification state of the heterologous bait polypeptide, i.e., either there is only or, preferentially, binding with modification or there is only or, preferentially, binding without modification. The modification state can be, as a non-limiting example, the presence or absence of phosphorylation, acetylation, acylation, methylation, ubiquitinilation or glycosylation, or occurrence of proteolytic cleavage or not. Preferably, the modification state is presence or absence of phosphorylation. The recombinant receptor can be a chimeric receptor in which the ligand-binding domain and the cytoplasmic domain are derived from two different receptors. Preferentially, the receptor is a multimerizing receptor. As described above, the cytoplasmic domain of the recombinant receptor comprises a heterologous bait polypeptide which can be fused to the carboxyterminal end or can replace a part of this carboxyterminal end or can be situated in the cytoplasmic domain itself as an insertion or a replacement of an endogenous internal fragment. In the case of a heteromultimerizing receptor, not all the chains need to comprise the bait, but it is sufficient if one of the composing chains does comprise the bait in its cytoplasmic domain.

The modification of the bait may be either in cis or in trans, i.e., by an enzymatic activity that is situated on the same cytoplasmic domain as the bait or by an enzymatic activity that is not linked to the receptor, such as an enzyme that circulates freely in the cytosol. Alternatively, in the case of a multimeric receptor, the modification may be carried out by an enzymatic activity that is situated on the cytoplasmic domain of another receptor chain than the one carrying the bait. The enzymatic activity may be part of the receptor chain or it may be an enzyme that binds to the receptor chain. Preferentially, the modification of the bait is induced by binding of a ligand to the ligand-binding domain. One preferred embodiment is a homodimerizing receptor in which the bait is phosphorylated by the inherent kinase activity of the cytoplasmic domain, preferentially a Jak kinase that is binding to the cytoplasmic domain. Another preferred embodiment is a heteromultimerizing receptor where the cytoplasmic domain of one chain comprises a bait to be modified and the cytoplasmic domain of another chain comprises the modifying activity.

Activation of the receptor and of the signaling pathway is achieved by binding of a ligand to the ligand-binding domain and by disruption of the binding of a prey polypeptide to the heterologous bait polypeptide situated in the cytoplasmic domain of the receptor. Preferentially, binding of the prey polypeptide is dependent upon the modification state of the heterologous bait polypeptide, which means that binding occurs only in the case where the bait is modified or only in the case where the bait is not modified.

It is another aspect of the invention to provide a prey polypeptide, whereby the prey polypeptide is a fusion protein comprising a polypeptide that can interact directly or indirectly with a bait polypeptide and another polypeptide that comprises an inhibitor of the activation of the receptor and/or a recruitment site for an inhibitor of the activation of the receptor. The inhibitor of the activation of the receptor can be an inhibitor of the activation site or an inhibitor of the signaling pathway. The inhibitor of the activation site of the receptor is preferentially an inhibitor of phosphorylation, more preferentially an inhibitor of tyrosine phosphorylation. One preferred embodiment is a prey polypeptide, whereby the inhibitor is a protein tyrosine phosphatase (PTP) or a functional part thereof. Another preferred embodiment is a prey polypeptide, whereby the inhibitor is a member of the Suppressor Of Cytokine Signaling (SOCS) family or a functional part thereof. Most preferentially, the inhibitor is SOCS1 or SOCS3 or a functional part thereof. The inhibitor of the signaling pathway of the receptor is preferentially an inhibitor of phosphorylation. One preferred embodiment is an inhibitor of the signaling pathway of the receptor, whereby the inhibitor is a JAK phosphatase.

Another preferred embodiment is an inhibitor of the signaling pathway of the receptor, whereby the inhibitor is a STAT phosphatase. Still another preferred embodiment is an inhibitor of the signaling pathway of the receptor, whereby the inhibitor is a Protein Inhibitor of Activated STAT (PIAS), preferably PIAS 3 (Chung et al., 1997).

Direct interaction means that there is a direct protein-protein contact between the heterologous bait polypeptide and the prey polypeptide. Indirect interaction means that the heterologous bait polypeptide interacts with one or more other compounds to form a complex that interacts with the prey polypeptide or vice versa. In the latter case, the prey polypeptide may interact either with only one or with several compounds from the complex. Preferably, the compounds are polypeptides. However, alternatively, the binding may be realized by one or more nonpolypeptidic compounds or a mixture of one or more polypeptides with one or more nonpolypeptidic compounds that bind to the bait and/or prey. Alternatively, a compound may bind to either the bait or the prey, changing its binding affinity, e.g., by a change of conformation, and enabling in this way the binding of the bait and the prey. The binding of the prey polypeptide to the bait polypeptide may be dependent upon the modification state of the bait polypeptide and/or of proteins within the binding complex.

In the case where disruptions of interactions of nuclear proteins are studied, the prey polypeptide may comprise a Nuclear Export Sequence (NES) to ensure that it is available in the cytosol. The NES signal (amino acids 37-46) of the heat stable inhibitor of the cAMP-dependent protein kinase has been shown to override a strong nuclear localization signal (Wiley et al., 1999). This NES will keep the prey polypeptide in the cytoplasm even if it has a strong nuclear localization signal, facilitating the interaction with the bait.

One preferred embodiment is a prey polypeptide according to the invention, whereby the prey polypeptide interacts with the heterologous bait polypeptide of a recombinant receptor according to the invention. Upon binding of a ligand to the ligand-binding domain and upon direct or indirect interaction of the heterologous bait polypeptide with the prey polypeptide, the inhibitor of the prey polypeptide will inhibit the modification of the activation site by modifying enzyme activity inherent to the cytoplasmic domain of the receptor and so inhibit the activation of the receptor. Preferentially, the inhibitor is an inhibitor of phosphorylation, the activation site is a phosphorylation site and the modifying enzyme activity is a kinase activity. More preferentially, the activation of the receptor comprises binding of a STAT polypeptide to the phosphorylated phosphorylation site, followed by phosphorylation of the STAT polypeptide and subsequent dimerization of two phosphorylated STAT molecules.

Another aspect of the invention is a vector, encoding a recombinant receptor according to the invention and/or a vector, encoding a prey polypeptide according to the invention. The recombinant receptor and the prey polypeptide may be situated on one or on separated vectors. The vector can be any vector known to the person skilled in the art including, but not limited to, episomal vectors, integrative vectors and viral vectors.

Another aspect of the invention is a eukaryotic cell comprising a recombinant receptor according to the invention. Preferentially, the eukaryotic cell is obtained by transformation or transfection with one or more vectors according to the invention. The eukaryotic cell comprises, but is not limited to, yeast cells, fungal cells, plant cells, insect cells and mammalian cells. Preferentially, the eukaryotic cell is a mammalian cell.

Still another aspect of the invention is a kit comprising one or more cloning vectors allowing the construction of one or more vectors according to the invention. It is clear for the people skilled in the art that a cloning vector encoding a recombinant receptor in which the part encoding for the cytoplasmic domain comprises one or more restriction sites, allowing an "in frame" fusion of a nucleic acid fragment encoding a polypeptide, can easily be used to construct a vector encoding a recombinant receptor according to the invention. In a similar way, a cloning vector encoding a first polypeptide comprising at least one inhibiting domain and/or a recruitment site for an inhibitor, such as a SOCS or SHP recruitment site, comprising one or more restriction sites allowing an "in frame" fusion of a nucleic acid encoding a second polypeptide with the first polypeptide can easily be used to construct a vector encoding a prey polypeptide according to the invention. Alternatively, both for the construction of the vector encoding the recombinant receptor and for the vector encoding the prey polypeptide, other cloning strategies known to the person skilled in the art may be used.

Still another aspect of the invention is a method of screening compounds disrupting compound-compound binding using a recombinant receptor and/or a prey polypeptide according to the invention. In a preferred embodiment, a eukaryotic cell carrying a recombinant receptor according to the invention and a prey polypeptide according to the invention is treated with a compound library. Disruption of bait-prey binding will result in an activation of the signaling pathway and can be detected by the use of a reporter system. The compound library may be added as extracellular compounds of the cell or may be produced within the cell as peptides or polypeptides, possibly after transformation or transfection of the cell with a library encoding the peptides or polypeptides.

One specific embodiment of the method of screening compounds disrupting compound-compound binding is a method whereby the binding is a protein-protein interaction. Another specific embodiment is a method of screening compounds disrupting protein-protein interaction, whereby the interaction is modification state dependent. The compound may be, as a nonlimiting example, an inhibitor of the modification in the case of a modification-dependent protein-protein interaction or a bait modifying enzyme in the case where the protein-protein interaction occurs only, or preferentially, in absence of modification. Still another specific embodiment is a method of screening compounds disrupting compound-compound binding, whereby the binding is mediated by three or more partners. In this case, one or more partners may not be or not completely be of a proteinaceous nature. It is clear for a person skilled in the art that a recombinant receptor, according to the invention, may, as a non-limiting example, bind to a small molecule. On the other hand, the prey polypeptide, according to the invention may also bind to the small molecule so that bait and prey are linked together by the small molecule. The small molecule may be present in the host cell as a compound produced by the cell itself or as a compound that is taken up from the medium.

Preferably, the method of screening compounds that disrupt compound-compound binding comprises the construction of a eukaryotic cell comprising a recombinant receptor according to the invention and a prey polypeptide according to the invention. The cell is brought into contact with a compound library that is added as extracellular compounds taken up by the cell or that is produced within the cell after transformation of the cell with a DNA library encoding the compounds. The disruption of the compound-compound binding is detected by the activation of the receptor, leading to an active signaling pathway, resulting in the induction of a reporter system. A reporter system can be any system that allows the detection and/or the selection of the cells carrying a recombinant receptor according to the invention. It is clear for the person skilled in the art that several reporter systems can be used. As a nonlimiting example, a luciferase gene, an antibiotic resistance gene or a cell surface marker gene can be placed after a promoter that is induced by the signaling pathway. Alternatively, reporter systems may be used that are based on the change in characteristics of compounds of the signaling pathway, when the pathway is active, such as the phosphorylation and/or dimerization of such compounds.

1. pSEL1-ALK4 (1 µg)+pMET7mcs (1 µg)+pXP2d2-rPAP1-luci (200 ng)+pUT651 (25 ng)
2. pSEL1-ALK4 (1 µg)+pMG2-FKBP12 (1 µg)+pXP2d2-rPAP1-luci (200 ng)+pUT651 (25 ng)
3. pSEL1-p53 (1 µg)+pMG2-FKBP12 (1 µg)+pXP2d2-rPAP1-luci (200 ng)+pUT651 (25 ng)

Luciferase activity was measured in triplicate.

NC: negative control, without ligand. EPO: stimulation of the receptor by EPO addition.

Figure 4:
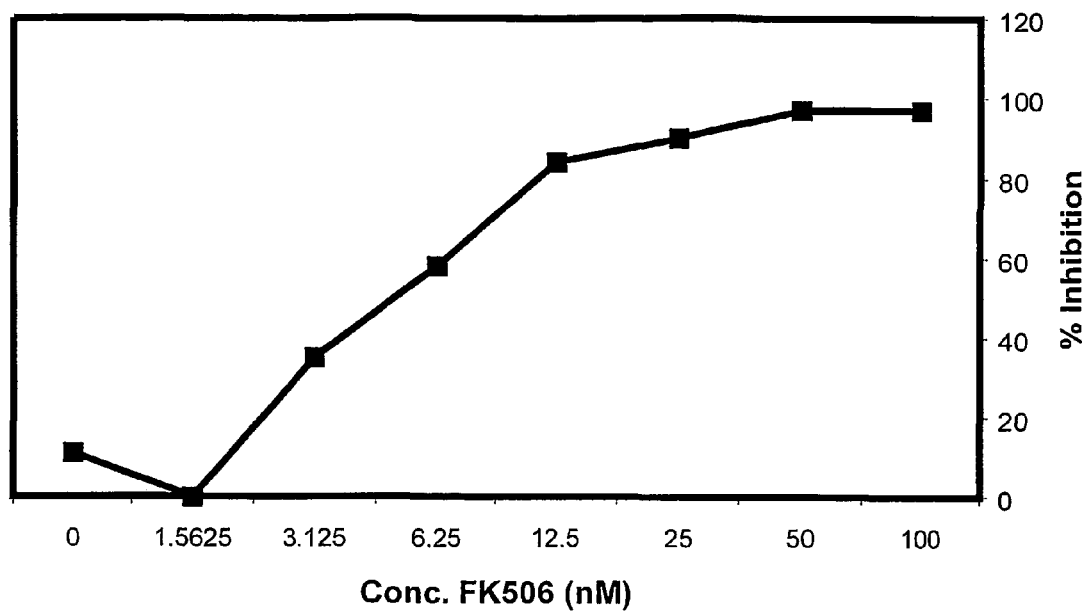

FIG. 4: Inhibition of the ALK4-FKBP12 interaction, in function of the FK506 concentration added to the medium.

Figure 5:
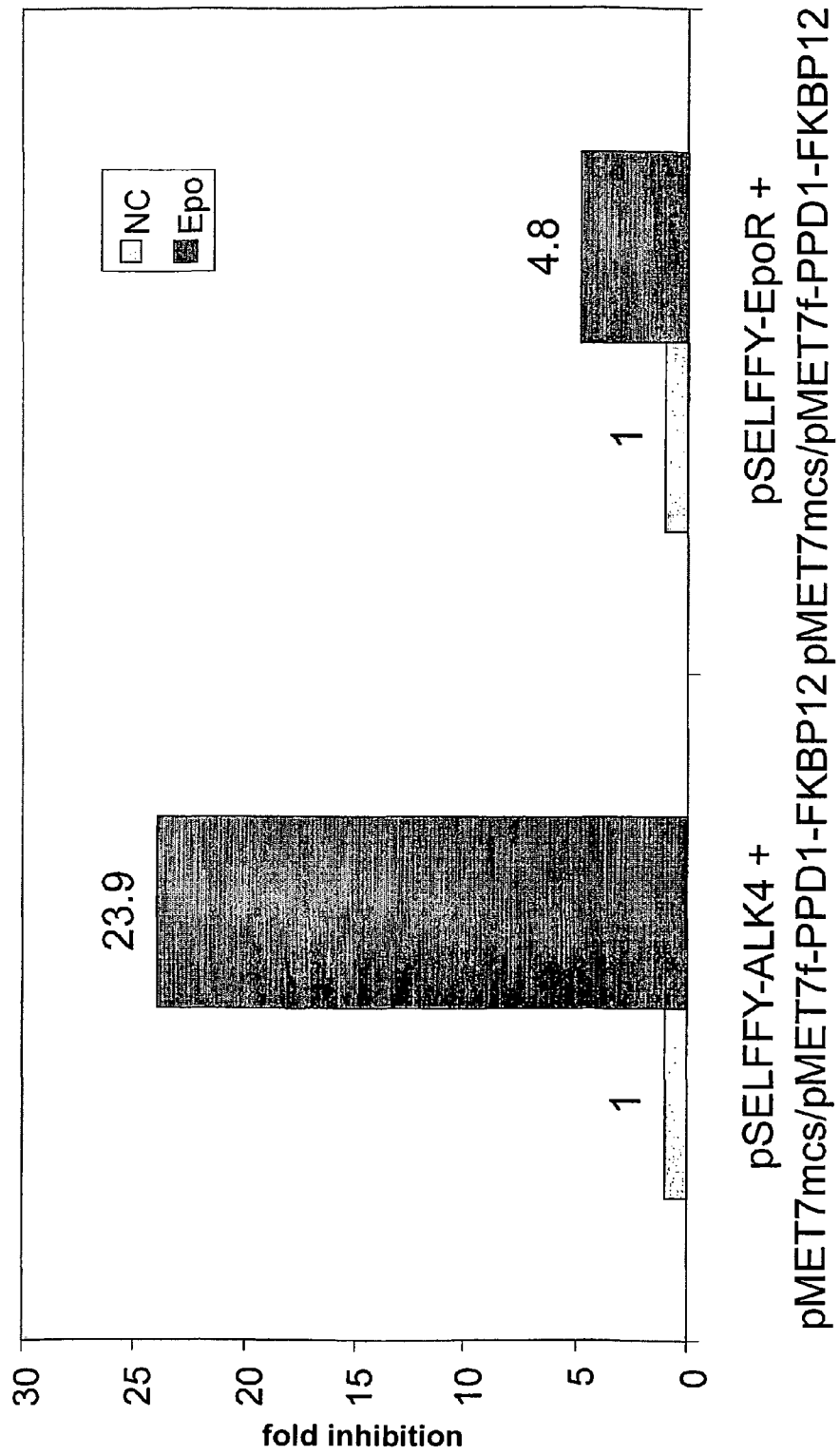

FIG. 5: Inhibition of pSELFFY bait constructs via the inhibitory prey pMET7-fPPD1-FKBP12, as measured by luciferase activity of the reporter gene and expressed as fold inhibition of the activity, compared to a mock transfection (pMET7mcs/pMET7-fPPD1-FKBP12; exp1/exp2 and exp3/exp4). HEK293T cells (six-well plate) were transfected with a combination of the following plasmids:

1. pSELFFY-ALK4 (1 µg)+pMET7mcs (1 µg)+pXP2d2-rPAP1-luci (200 ng)+pUT651 (25 ng)
2. pSELFFY-ALK4 (1 µg)+pMET7-fPPD1-FKBP12 (500 ng)+pMET7mcs (500 ng)+pXP2d2-rPAP1-luci (200 ng)+pUT651 (25 ng)
3. pSELFFY-EpoR (1 µg)+pMET7mcs (1 µg)+pXP2d2-rPAP1-luci (200 ng)+pUT651 (25 ng)
4. pSELFFY-EpoR (1 µg)+pMET7-fPPD1-FKBP12 (500 ng)+pMET7mcs (500 ng)+pXP2d2-rPAP1-luci (200 ng)+pUT651 (25 ng)

Luciferase activities were measured in triplicate. A representative experiment is shown.

NC: negative control, without ligand. EPO: stimulation of the receptor by EPO addition.

Figure 6:
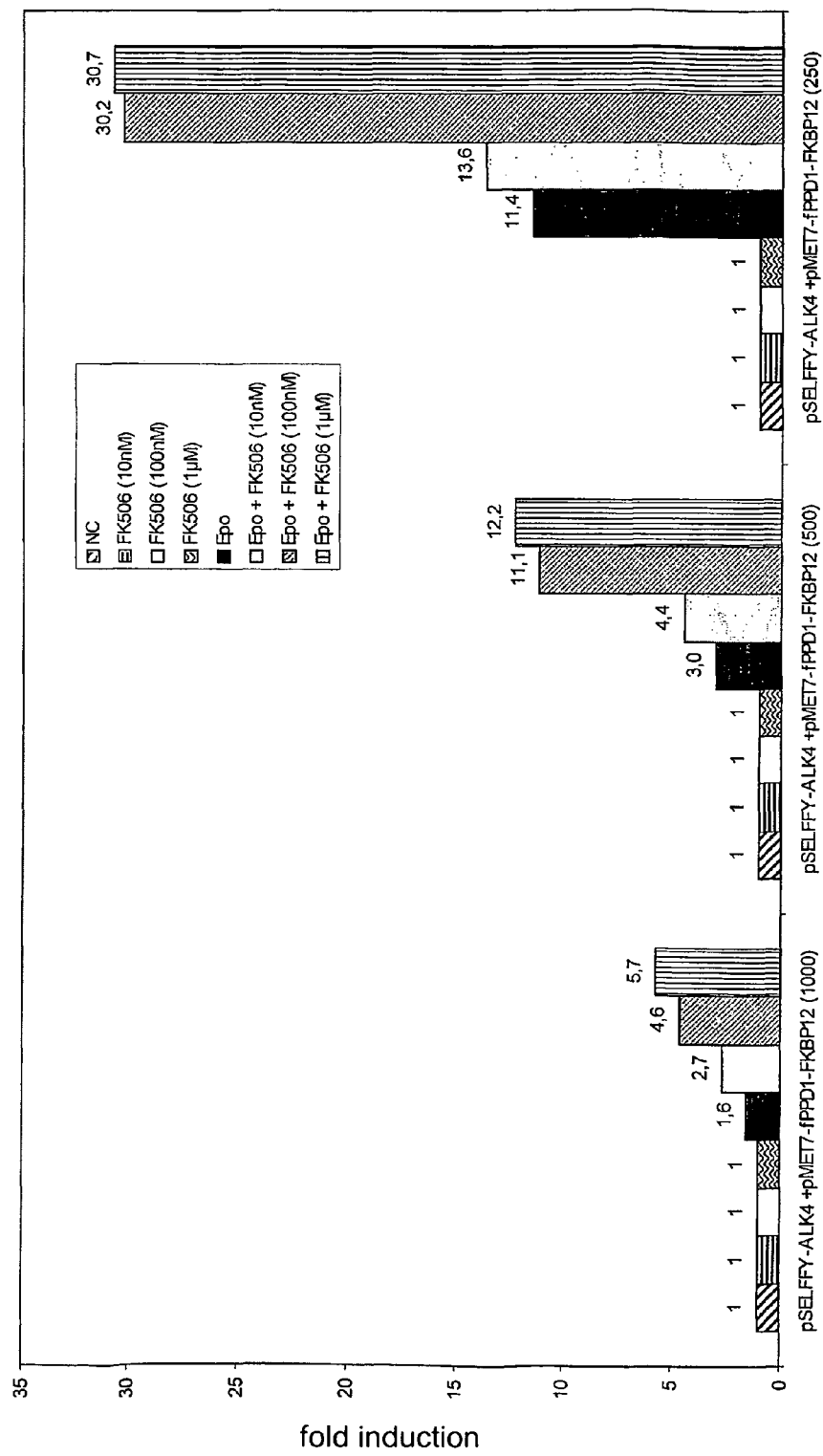

FIG. 6: FK506 partially restores signaling via the pSELFFY-ALK4 bait, as measured by the luciferase activity of the reporter gene. HEK293T cells (six-well plate) were transfected with a combination of the following plasmids:

1. pSELFFY-ALK4 (1 ng)+pMET7-fPPD1-FKBP12 (1 µg)+pXP2d2-rPAP1-luci (200 ng)+pUT651 (25 ng)
2. pSELFFY-ALK4 (1 ng)+pMET7-fPPD1-FKBP12 (500 ng)+pMET7mcs (500 ng)+pXP2d2-rPAP1-luci (200 ng)+pUT651 (25 ng)
3. pSELFFY-ALK4 (1 ng)+pMET7-fPPD1-FKBP12 (250 ng)+pMET7mcs (750 ng)+pXP2d2-rPAP1-luci (200 ng)+pUT651 (25 ng)
4. pSELFFY-EpoR (1 ng)+pMET7-fPPD1-FKBP12 (1 ng)+pXP2d2-rPAP1-luci (200 ng)+pUT651 (25 ng)
5. pSELFFY-EpoR (1 µg)+pMET7-fPPD1-FKBP12 (500 ng)+pMET7mcs (500 ng)+pXP2d2-rPAP1-luci (200 ng)+pUT651 (25 ng)
6. pSELFFY-EpoR (1 µg)+pMET7-fPPD1-FKBP12 (250 ng)+pMET7mcs (750 ng)+pXP2d2-rPAP1-luci (200 ng)+pUT651 (25 ng)

A representative experiment of triplicate luciferase measurements is shown. The values have been normalized using background luciferase activities (fold induction) and by using an irrelevant bait construct (pSELFFY-EpoR, exp. 4-6) to correct for toxicity of FK506 on the cells.

NC: negative control, without ligand. EPO: stimulation of the receptor by EPO addition. FK506: interaction inhibitor FK506 is added (concentration as indicated). Epo+FK506: both Epo and FK506 (concentration as indicated) are added. (1000), (500) and (250) refers to the amount in ng of pMET7-fPPD1-FKBP12 used in the transfection experiment.

DETAILED DESCRIPTION OF THE INVENTION

The following definitions are set forth to illustrate and define the meaning and scope of various terms used to describe the invention herein.

"Receptor" as used herein does not necessarily indicate a single polypeptide but may indicate a receptor complex consisting of two or more polypeptides and comprising a ligand-binding domain and a cytoplasmic domain. Recombinant receptor means that at least one of the polypeptides is recombinant. Preferably, the polypeptide comprising the cytoplasmic domain is recombinant. "Cytoplasmic domain" as used herein includes the transmembrane domain.

"Inhibition of activation" of a receptor by binding of a prey polypeptide to a heterologous bait peptide is every action by which a receptor that is activated in absence of the binding shows a significantly reduced induction of its signaling pathway, as measured by the reduced output of the reporter system, independent of the mechanism used. This can be, as a nonlimiting example, by inhibition of the modifying enzyme activity, by blocking of the activation site, or by inhibition of binding of one of the compounds of the signaling pathway. Reduced induction is any reduction of induction that can be measured in a reliable way, by comparing the situations of binding and absence of binding. Preferentially, the induction of signaling is ligand dependent. However, alternatively, a ligand-independent constitutive signaling receptor may be used. For specific cases, inhibition of activation is referred to as "inhibition of the activation site" or "inhibition of the signaling pathway."

"Reporter system" as used herein may be any system known to the person skilled in the art that results in a detectable output upon activation of the receptor. As some nonlimiting examples, cell survival or luciferase activity may be used.

"Activation site" of a receptor is the site that, in the wild-type receptor, is modified after binding of a ligand to the ligand-binding domain, leading to a clustering and/or reorganization of the receptor and subsequent activation of the modifying enzyme activity and to which a compound of the signaling pathway can bind after modification, or any site that can fulfill a similar function. In the latter case, the activation site is not necessarily located on the same polypeptide as in the wild-type receptor, but may be situated on another polypeptide of the receptor complex.

"Modifying enzyme activity" as used herein means the enzymatic activity associated to or incorporated in the cytoplasmic domain of the receptor that is induced upon binding of the ligand to the ligand-binding domain and subsequent reorganization of the receptor (e.g., by a conformational change) and may modify the activation site. Preferably, the activation site is a phosphorylation site and the modifying enzyme activity is a kinase activity.

"Activation of a receptor" as used herein means that the receptor is inducing a signaling pathway by binding of a compound of the signaling pathway to the modified activation site, whereby the activation normally results in the induction or repression of one or more genes. The gene is preferentially a reporter gene which allows monitoring the activation of the receptor. An "activated receptor" is a receptor where the binding of a compound to the activation site has been enabled by modification of the site.

"Multimerizing receptor" as used herein means that the activated receptor comprises several polypeptides. It does not necessarily imply that the multimerization is induced by ligand binding: the receptor can exist as a preformed complex of which the conformation is changed upon ligand binding.

"Polypeptide" as used herein means any proteinaceous structure, independent of the length, and includes molecules such as peptides, phosphorylated proteins and glycosylated proteins. Polypeptide as used herein is not necessarily indicating an independent compound but can also be used to indicate a part of a bigger compound, such as a domain of a protein.

"Heterologous bait polypeptide" as comprised in the receptor means that within the receptor or fused to the receptor, but not in the ligand-binding domain of the receptor, there is a polypeptide that is not present in the nonrecombinant receptor of which the cytoplasmic domain of the chimeric receptor is derived. In the case of a transmembrane receptor, the heterologous bait is fused within the cytoplasmic domain or fused to the cytoplasmic domain. The heterologous bait may replace a part of the cytoplasmic domain. "Bait" herein means that this polypeptide can interact with other polypeptides not belonging to the normal receptor complex.

"Prey polypeptide" as used herein means a fusion protein comprising a polypeptide that can bind with the heterologous bait polypeptide and a polypeptide that comprises an inhibitor of the receptor and/or a recruitment site for an inhibitor of the receptor, i.e., every polypeptide that can directly or indirectly inhibit the activation of the receptor according to the definition above.

"Ligand" means every compound that can bind to the ligand-binding domain of a receptor and that is able to initiate the signaling pathway by binding to the ligand-binding domain. "Initiating" as used herein means starting the events that normally follow the binding of the ligand to the ligand-binding domain of a receptor, e.g., multimerization for a multimerizing receptor, but it does not imply activation of the receptor and/or accomplishing of the signaling pathway.

"Functional part of an inhibitor," such as a functional part of SHP or SOCS, means any part that can still fulfill its inhibiting activity. In the case of a protein phosphatase, it is a part that still shows protein phosphatase activity.

"Compound" means any chemical or biological compound, including simple or complex organic or inorganic molecules, peptides, peptido-mimetics, proteins, antibodies, carbohydrates, nucleic acids or derivatives thereof.

"Bind" or "binding" means any interaction, be it direct or indirect. A direct interaction implies a contact between the binding partners. An indirect interaction means any interaction whereby the interaction partners interact in a complex of more than two compounds. This interaction can be completely indirect, with the help of one or more bridging compounds, or partly indirect, where there is still a direct contact that is stabilized by the interaction of one or more compounds.

"Cloning vector" is a vector that is generally considered as an intermediate step for the construction of another vector. It is intended to insert one or more nucleic acid fragments in order to obtain one or more new vectors that will be used to transform the host cell of interest.

The invention is further explained with the aid of the following illustrative examples.

EXAMPLES

Materials and Methods of the Examples

Cell Lines and Transfection Procedure

Transfections were performed according to the calcium phosphate method (Graham and van der Eb, 1973).

Recombinant human erythropoietin (Epo) was purchased from R&D Systems. Typical stimulation conditions were 5 ng/ml Epo.

HEK293T cells were maintained in a 10% $CO_2$ humidified atmosphere at 37° C., and were grown using DMEM with 4500 mg/ml glucose, 10% fetal bovine serum and 50 µg/ml gentamycin (all from Life Technologies).

Construction of the Plasmids

Generation of the pSEL1

The mutant leptin receptors (Eyckerman et al., 1999) Y985-1077F and Y985-1077-1138F (LepR-F3) were generated using the Quikchange™ site-directed mutagenesis procedure using Pfu polymerase (Stratagene) on the pMET7-LepR template. Mutagenic oligonucleotides were MBU-O-157, MBU-O-158, MBU-O-159, MBU-O-160, MBU-O-161 and MBU-O-162. Each single mutation was coupled to a change in restriction cleavage and was confirmed by restriction and DNA sequence analysis. The double and triple mutants were created using a sequential approach. PCR amplification on this pMET7-LepR-F3 vector template using MBU-O-447 and MBU-O-448 as forward and reverse primers, respectively, resulted in a LepR-F3 amplicon spanning the transmembrane and intracellular domains of LepR-F3 (+1 extra Gly of the extracellular part), which was subcloned in the pCR®-Blunt vector (Invitrogen). PacI-SacI digestion of the resulting plasmid yielded a DNA fragment containing the LepR-F3 sequence, which was ligated into PacI-SacI digested and gel-purified pSV-SPORT-EpoR/IFNaR2-2 vector (Pattyn et al., 1999). This resulted in the pSV-SPORT-EpoR/LepR-F3, which was renamed to pSEL1.

Construction of pSELI-EpoR

RNA was prepared from $5 \times 10^6$ TF-1 cells using the RNeasy kit (Qiagen), and eluted in 50 µl water from which 10 µl was used as input for RT-PCR. Standard RT-PCR was performed as follows: 2 µl (2 µg) of oligodT (12-18 mer; Pharmacia) was added and incubated at 70° C. for 10 minutes, the reaction mixture was chilled on ice for 1 minute, cDNA was prepared by adding 4 µl of 10×RT buffer (Life Sciences), 1 µl 20 mM dNTPs (Pharmacia), 2 µl 0.1 M DTT, and 1 µl of MMLV reverse transcriptase (200 U; Superscript RT; Life Technologies) to an end volume of 20 µl. Incubations were as follows: RT for 10 minutes, 42° C. for 50 minutes, 90° C. for 5 minutes, and 0° C. for 10 minutes. Following this, 0.5 µl RnaseH (2 U; Life Technologies) was added and the mixture was incubated at 37° C. for 20 minutes, followed by chilling on ice. PCR on this cDNA was performed using Pfu enzyme (5 U; Stratagene). An intracellular fragment of the human EpoR (amino acids 370-453) was amplified from 4 µl TF1 cDNA using MBU-O-675 and MBU-O-676 as forward and reverse primers, respectively, with two consecutive PCR reactions and an intermediate gel-purification. SacI and XbaI recognition sites are present in the forward and reverse primers, respectively. The reverse primer also encodes a stop codon. After gel-purification of the PCR amplicon band of the correct size, the fragment was subcloned in pCR®-Blunt, digested with SstI (which has the same recognition site as SacI) and XbaI, and ligated into SstI-XbaI digested and gel-purified pSEL1 vector, resulting in the pSEL1-EpoR construct.

Construction of pSEL1-p53

A DNA fragment encompassing murine p53 was amplified with MBU-O-450 and MBU-O-451 using the p53 control plasmid from the HybriZAP-2.1 Two-Hybrid cDNA synthesis kit (Stratagene) as template. The forward primer contains an SalI restriction site that allows in-frame coupling to the EpoR/LepR-F3 hinge construct. The reverse primer contains a STOP codon and a XbaI restriction site. The 243 amino acid-long p53 fragment (amino acids 73-315) contains the interaction site with SVT, but lacks the nuclear targeting signal and the oligomerization domain. Subcloning over pCR®-Blunt, digestion with SalI-XbaI and gel-purification yielded a fragment that was ligated into SalI-XbaI cut and gel-purified pSEL1 vector, resulting in pSEL1-p53.

Construction of pSEL1-ALK4

The pSEL1-ALK4 construct was generated by cutting the pSEL1 plasmid with SalI, followed by incubation with Klenow fragment to polish the sticky ends. The cytoplasmic tail of the ALK4 (Activin receptor Like Kinase 4; aa 150-337; ten Dijke et al., 1993) receptor was cut from pGAD424-ALK4 (gift from Prof. D. Huylebroeck) via EcoRI-BamHI, subsequently polished with Klenow fragment and ligated in the digested pSEL1 vector. The construct was named pSEL1-ALK4.

Construction of pSV-EpoR-Lep RFFY-EpoR (=pSELFFY-EpoR)

pSV-EpoR-LepRFFY(=pSELFFY) was generated by amplifying the transmembrane and the intracellular part of the murine leptin receptor containing the Y985F and the Y1077F mutations by using primers MBU-O-447 and MBU-O-448 and the pMET7-LepRFFY construct (Eyckerman et al., 1999) as template. The forward primer contains a PacI site allowing in-frame fusion with the extracellular part of the erythropoietin receptor. The reverse primer contains SalI, SstI, NotI and XbaI sites. The LepRFFY fragment was cloned in pSEL1-EpoR via a PacI-SstI based exchange, preceded by a subcloning step in pCR-Blunt (Invitrogen). This leads to pSELFFY-EpoR.

Construction of pMET7-flag-gp130

The pMET7mcs vector is a modified version of pMET7 (Takabe et al., 1988) containing an expanded MCS by insertion of the extra unique BglII, EcoRV, BstEII, AgeI and XhoI restriction sites. PCR amplification on the pSVL-gp130 template using the forward primer MBU-O-586 and the reverse primer MBU-O-443 generated a DNA fragment encoding a 158 amino acid-long intracellular fragment of the human gp130 chain, which contains 4 STAT-3 association motifs (amino acids 761-918, the stop codon was not co-amplified). The forward primer contains from 5' to 3' an ApaI restriction site, a Kozak consensus sequence, a flag-tag encoding sequence (Met-Asp-Tyr-Lys-Asp-Asp-Asp-Asp-Lys-Ile (SEQ ID NO:34)), and a BglII restriction site. The reverse primer encodes an additional hinge sequence (Gly-Gly-Ser) and contains an EcoRI recognition site. ApaI and EcoRI digestion of the PCR product (after subcloning in pCR-Blunt) and of pMET7-mcsA, allowed us to ligate the gp130 fragment into the pMET7 vector, generating the pMET7-flag-gp130 construct.

Construction of pMG1-SVT

SV40 largeT antigen (SVT) was amplified using a vector from the HybriZAP-2.1 Two-Hybrid cDNA synthesis kit (Stratagene, pSV40) as template. Primers MBU-O-445 and MBU-O-446 were used to generate a DNA fragment encoding 448 amino acids between residues 261 and 708. The N-terminal deletion eliminates the nuclear targeting signal in SVT. The forward primer contains an EcoRI recognition site that allows in-frame ligation to the gp130-hinge sequence. The reverse primer contains additional NruI, XhoI, BglII, NotI and XbaI restriction sites and also encodes the stop codon after the SVT coding sequence. Subcloning in pCR®-Blunt, followed by recovery of the cleaved amplicon with EcoRI and XbaI, allowed ligation in the EcoRI-XbaI opened pMET7-flag-gp130 vector, yielding pMET7-flag-gp130-SVT, which was renamed pMG1-SVT.

Construction of pMG1-CIS

The complete coding region for mouse Cytokine Inducible SH2-containing protein CIS (amino acids 2-257) was amplified using MBU-O-677 and MBU-O-678 as forward and reverse primers, respectively. The forward primer contains an EcoRI recognition site and the reverse primer contains an XbaI recognition site and the stop codon. The amplified and gel-purified fragment was subcloned into the pCR®-Blunt vector (Invitrogen). The insert was recovered by EcoRI and XbaI digestion and gel-purification and was cloned into an EcoRI-XbaI digested and gel-purified pMG1-SVT vector, leading to the pMG1-CIS vector.

Construction of pMET7-fSOCS3

Prey constructs were generated in the pMET7 vector, which contains the strong constitutive SRα promoter (Takebe et al., 1988). Rat SOCS3 cDNA was amplified using MBU-O-302 and MBU-O-303 as forward and reverse primers, respectively, and using mRNA from leptin-stimulated PC12 cells (rat pheochromocytoma cell line) as a template. cDNA was prepared using a standard RT procedure with Superscript Reverse Transcriptase (Life Technologies). Amplification was performed using Pfu polymerase (Stratagene). The complete SOCS3-coding fragment was reamplified using forward primer MBU-O-837 and the reverse primer described above, which allows BglII-XbaI-based cloning in pMG1-CIS, resulting in an expression vector wherein the complete coding sequence of SOCS3 is N-terminally fused to a FLAG tag sequence (MDYKDDDDK (SEQ ID NO:35)). This construct was named pMET7-fSOCS3.

Construction of pMET7-fSOCS3 CISSH2

Unique BspEI and XhoI sites were created by site-directed mutagenesis (Quikchange™ Site-Directed Mutagenesis Kit, Stratagene) in both the SOCS3 construct and the pMG1-CIS construct, while respecting the amino acid sequence. The BspEI site was created in front of the SH2 domain, while the XhoI site was inserted in front of the SOCS box sequence. Mutagenic primers for BspEI in SOCS3 were MBU-O-1005 and MBU-O-1006 as forward and reverse primers, respectively. Primers for insertion of the XhoI site in SOCS3 were MBU-O-1007 and MBU-O-1008. BspEI was created in pMG1-CIS using MBU-O-1001 and MBU-O-1002, while XhoI was created using MBU-O-1003 and MBU-O-1004.

The SOCS3 SH2 domain (amino acids 46-184) was swapped with the SH2 domain of CIS (amino acids 82-218), using a BspEI-XhoI-based exchange. This construct was named pMET7-fSOCS3 CISSH2.

The pMET7-fCIS construct was generated by cutting the pEF-FLAG-I/mCIS construct (obtained from N. Nicola) with EcoRI- and PvuII, and the pMG1-CIS construct with PvuII-KpnI. This results in two fragments of the CIS cDNA, which were simultaneously cloned in a three-fragment ligation step in the EcoRI-KpnI opened pMET7mcs construct.

The pEF-FLAG-I/SOCS2 construct expressing N-terminally flag-tagged full size murine SOCS2 was obtained from N. Nicola.

Other Constructions

Prey constructs were generated in the pMET7 vector, which contains a strong constitutive hybrid SRα promoter (Takebe et al., 1988).

The pMET7mcs vector is a modified version of pMET7 containing an expanded MCS by insertion of the extra unique BglII, EcoRV, BstEII, AgeI and XhoI restriction sites.

The pUT651 construct expressing β-galactosidase was obtained from Eurogentec. Generation of the pGL3-rPAP1-luci construct was described before (Eyckerman et al., 1999). The full-length rPAP1 promoter fragment was excised using partial digestion with KpnI and XhoI and ligated into the KpnI-XhoI digested pXP2d2 vector (gift from Prof. S. Nordeen), resulting in the leptin-responsive pXP2d2-rPAP1-luci reporter construct. The pXP2d2 vector is a derivative of pXP2 that lacks potential cryptic Activator Protein 1 sites (Grimm and Nordeen, 1999). All constructs were verified by restriction and sequence analysis.

Generation of the ALK4 bait and FKBP12 prey constructs

For the construction of the pMG2 vector, the MG1-SVT vector was digested with EcoRI and NotI, followed by incubation with Klenow fragment (Boehringer Mannheim) to polish the ends. This blunt-ended vector was incubated with Alkaline phosphatase (Boehringer Mannheim) to dephosphorylate the blunt ends. Cassette dB of the Gateway Vector Conversion System (Life Technologies) was then ligated into the opened vector leading to the pMG1-gateway vector. A PCR reaction using primers MBU-O-1094 and MBU-O-1076 on the pMG1-SVT template was performed, resulting in fragments that contain gateway recombination sites. This fragment also contains a part (amino acids 905-918) of the gp130 chain. The fragment was then cloned on the pMG1-gateway vector using a two-step gateway reaction (Life Technologies), resulting in pMG2-SVT. The pMG2-SVT construct was digested by EcoR1-XbaI and the vector was gel-purified.

Full-size FKBP12 (aa 2-107) was amplified with primers MBU-O-1250 and MBU-O-1251 on the pCMF2E (Ariad Pharmaceuticals) template. The amplicon was cloned in the pMG2-SVT vector via EcoRI-XbaI. The construction was named pMG2-FKBP12.

Generation of the Activator Bait Construct pSELFFY-ALK4

The intracellular domain of ALK4 (aa 150-337) was amplified using primers MBU-O-1261 and MBU-O-1262 on the pGAD424-ALK4 template. The amplicon was cloned in pSELFFY via SstI-NotI, resulting in the pSELFFY-ALK4 construct.

Generation of the inhibitory prey construct pMET7-fPPD1-FKBP12

Amplification of the phosphatase domain of PTP-1B (aa 1-276; Protein Tyrosine Phosphatase 1B, NCBI accession number P18031) was performed on template pGEX-PTP-1B (gift from R. Devos) using primers MBU-O-1465 and MBU-O-1466. The phosphatase domain was subcloned in pMG2-FKBP12 via BamHI and EcoRI, leading to the pMET7-fPPD1-FKBP12 construct.

Example 1

Specific Inhibition of Activation of the EpoR-LepRFFY-EpoR by the SOCS3 CISSH2 Chimera is Disrupted by Overexpression of SOCS2

The following combinations of plasmids were transfected in $4 \times 10^5$ HEK293T cells.
  a. pSV-EpoR-LepR FFY-EpoR+pMET7mcs+pXP2d2-rPAP1-luci+pUT651
  b. pSV-EpoR-LepR FFY-EpoR+pMET7-fSOCS3 CISSH2+pXP2d2-rPAP1-luci+pUT651
  c. pSV-EpoR-LepR FFY-EpoR+pMET7-fSOCS3 CISSH2+pEF-FLAG-I/SOCS2+pXP2d2-rPAP1-luci+pUT651
  d. pSV-EpoR-LepR FFY-EpoR pMET7-fCIS pXP2d2-rPAP1-luci+pUT651

Figure 1:
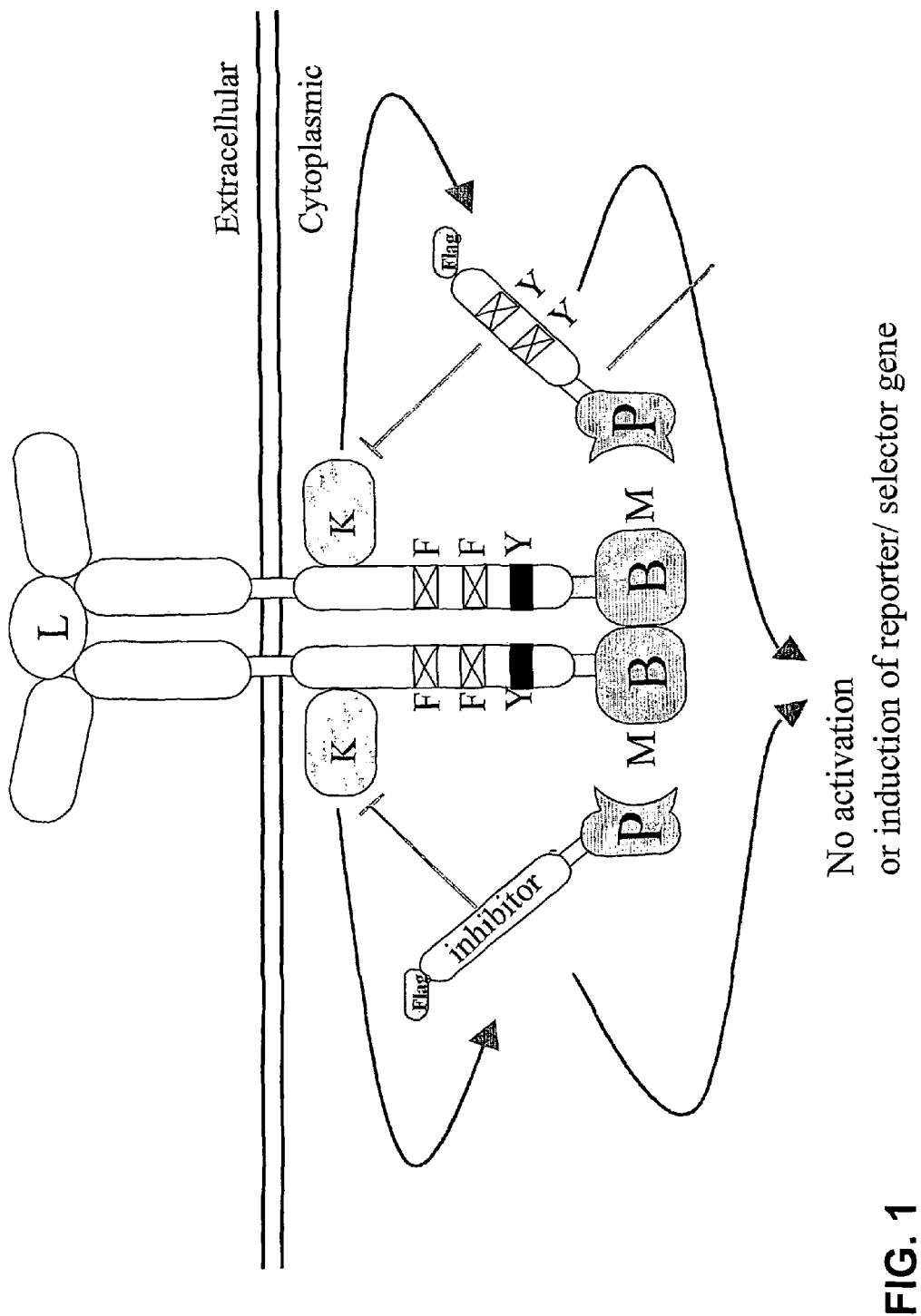
FIG. 1: Principle of the reversed mammalian protein-protein interaction trap. B: bait; K: modifying enzyme activity; L: ligand; M: possible modification of the bait; P: prey. F and Y represent the amino acids that function as a mutated (F) or functional (Y) receptor activation site or inhibitor recruitment site. The example illustrates a tyrosine phosphorylation site. As is shown in the figure, the bait-prey interaction may be modification dependent. The inhibitor, such as SOCS or a functional part thereof, is fused to the prey polypeptide, as illustrated at the left-hand side. Alternatively, an inhibitor recruitment domain, such as a SOCS or SHP recruitment domain, may be fused to the prey, as illustrated at the right-hand side. Both domains may be connected by a hinge region, such as a GGS sequence, to optimize the flexibility of the protein and the resulting negative feedback. The prey polypeptide may be fused to a "flag" sequence to facilitate identification and/or isolation, but this is not an essential feature.
Figure 2:
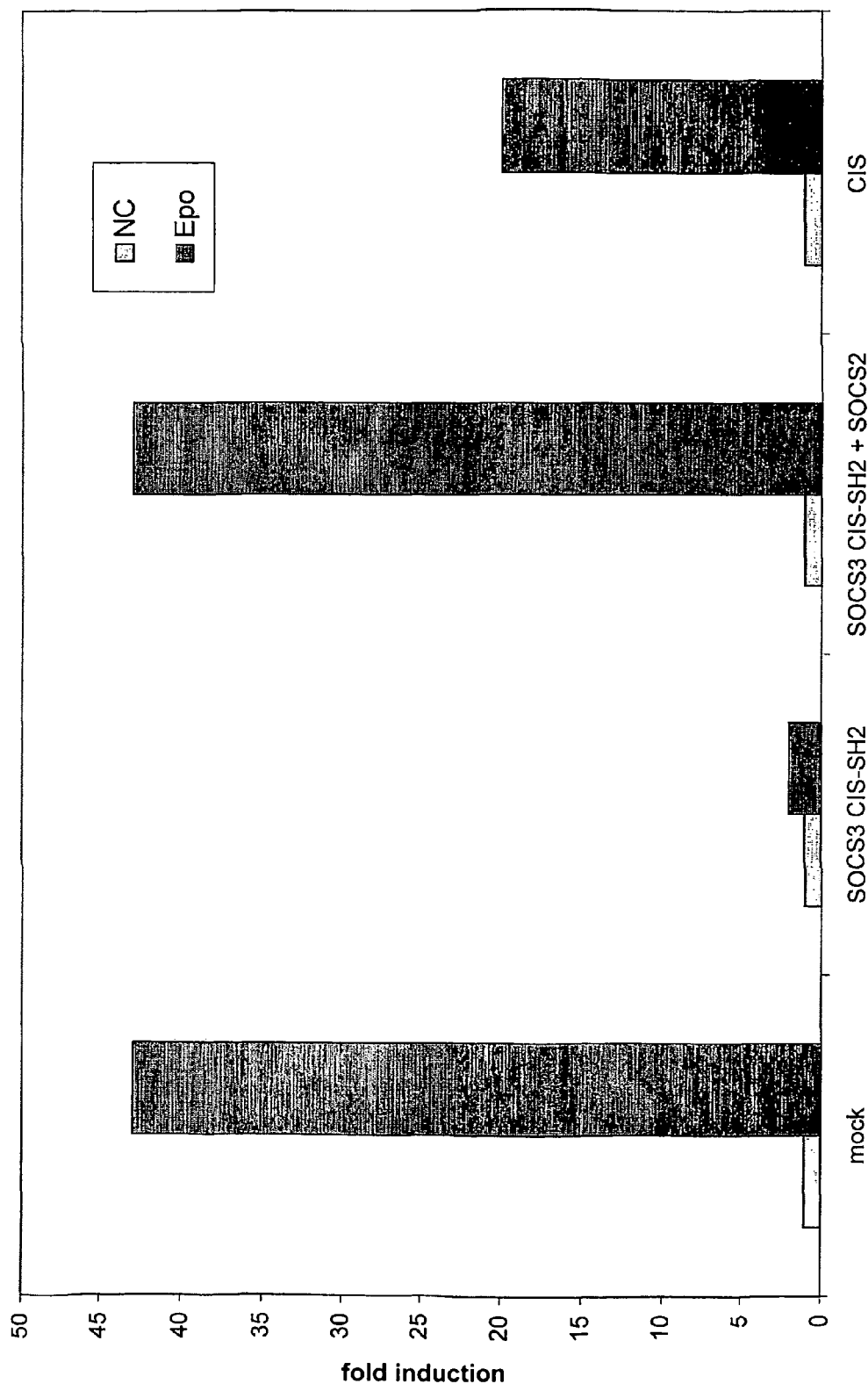
FIG. 2: Specific inhibition of activation of the EpoR-Lep-RFFY-EpoR by the SOCS3 CISSH2 chimera is disrupted by overexpression of SOCS2.

DNA amounts in a 300 µl precipitation mixture were: 1 µg pSV-EpoR-LepRFFY-EpoR chimeric receptor construct, 1 µg of pXP2d2-rPAP1-luci reporter construct, 25 ng of pUT651 for normalization and 100 ng of the other plasmids. Additional pMET7mcs vector was added to keep DNA amounts constant in the transfections. Two hundred µl of this precipitation mixture was added to $4 \times 10^5$ HEK293T cells in six-well plates. Twenty-four hours after transfection, cells were resuspended using Cell Dissociation Agent (Life Technologies) and seeded in black well plates. The seeded cells were stimulated for 24 hours with erythropoietin or were left unstimulated. Reporter activity was measured using a luciferase assay and a TopCount chemiluminescence counter (Can berra Packard). Results are shown in FIG. 2.

These results clearly show strong induction when the EpoR-LepRFFY-EpoR chimera is expressed. The induction is moderately inhibited by co-expression of the CIS wild-type protein, but shows very strong inhibition upon co-transfection of the chimeric SOCS3 CISSH2 protein. The SH2 domain targets the SOCS3 inhibitory regions towards the activated complex, resulting in specific inhibition. When the SOCS2 protein is co-expressed with the SOCS3 CISSH2 protein, inhibition is lost due to competition for the binding site, resulting in strong induction of the reporter gene.

Example 2

Disruption of the ALK4-FKB12 Interaction by FK506

To demonstrate the feasibility of the technique, a normal ALK4-FKB12 interaction, measured with a positive read-out receptor-based interaction trap (i.e., induction of the luciferase activity, by activation of a recombinant receptor comprising a ligand-binding domain and a cytoplasmic domain that comprises a heterologous bait polypeptide, whereby the receptor is activated by binding of a ligand to the ligand-binding domain and by binding of a prey polypeptide, fused to an activation domain to the heterologous bait peptide, as described in the European patent application 00201771.3) was inhibited by the addition of FK506.

The ALK4-FKBP12 interaction has been described by Wang et al. (1994).

To test the ALK4-FKBP12 interaction in the positive read-out receptor-based interaction trap, 400,000 HEK293T cells (six-well plate) with a combination of the following plasmids:

1. pSEL1-ALK4 (1 µg)+pMET7mcs (1 µg)+pXP2d2-rPAP1-luci (200 ng)+pUT651 (25 ng)
2. pSEL1-ALK4 (1 µg)+pMG2-FKBP12 (1 µg)+pXP2d2-rPAP1-luci (200 ng)+pUT651 (25 ng)
3. pSEL1-p53 (1 µg)+pMG2-FKBP12 (1 µg)+pXP2d2-rPAP1-luci (200 ng)+pUT651 (25 ng)

pMET7mcs was added as indifferent plasmid, to transfect each time with an equal amount of DNA.

Figure 3:
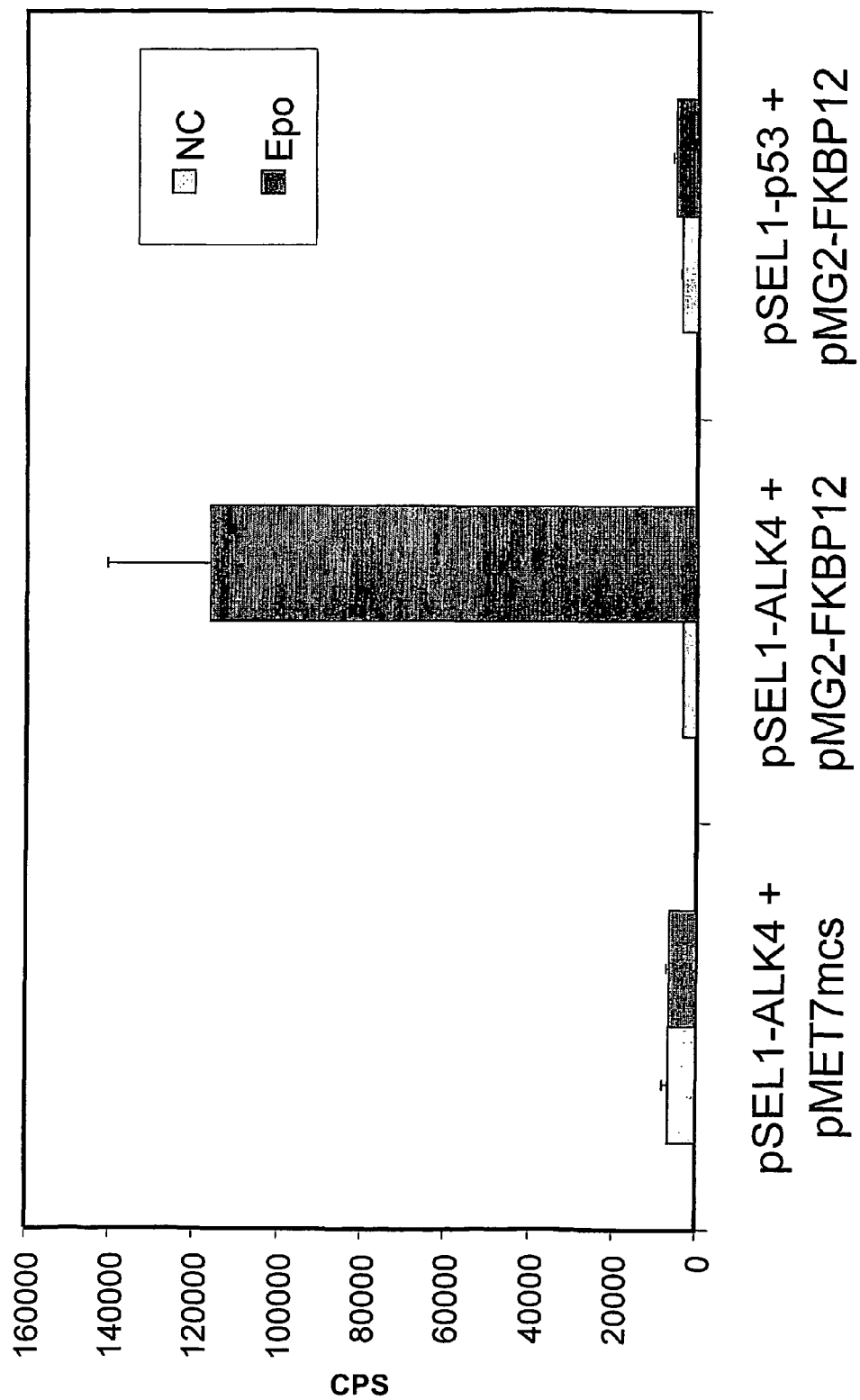
FIG. 3: ALK4 and FKBP12 interaction in HEK293T cells as measured by the luciferase activity of the reporter gene. HEK293T cells (six-well plate) were transfected with a combination of the following plasmids.

Two days after transfection, cells were seeded in black well plates (approximately 10,000 cells/well) and treated or not with Epo (5 ng/ml). Twenty-four hours after stimulation, rPAP1 and constitutive reporter (pUT651) activity was assayed by measuring luciferase and beta-galactosidase activity, respectively. A representative experiment is shown in FIG. 3. Luciferase activity was measured in triplicate. The experiment clearly shows that the reporter gene is only induced in the presence of two recombinant-binding partners ALK4 and EPO, and that no activity can be detected either in absence of the ligand of the receptor (EPO), nor in absence of one of the binding partners.

In a subsequent experiment, it was evaluated whether the interaction (and the positive read-out) could be inhibited by the addition of the ALK4-FKBP12 interaction inhibitor FK506. To this aim, 400,000 HEK293T cells (six-well plate) were transfected with a combination of the following plasmids:

pSEL1-ALK4(1 µg)+pMG2-FKBP12(1 µg)+pXP2d2-rPAP1-luci(200 ng)+pUT651(25 ng)

Two days after transfection, cells were seeded in black well plates (approximately 10,000 cells/well) and pretreated with a serial dilution of FK506 (as shown in FIG. 4). Epo was added after two hours to the treated cells (5 ng/ml). Twenty-four hours after stimulation, rPAP1 activity was measured. Luciferase activity was measured in triplicate. The results are shown in FIG. 4 and clearly indicate that the ALK4-FKBP12 protein-protein interaction, as measured in the positive read-out receptor-based interaction trap, can be completely blocked by the addition of the FK506.

Example 3

Expression of the pMET7-fPPD1-FKBP12 Inhibitory Prey leads to inhibition of Signaling Via the pSELFFY-ALK4 Bait and can be Blocked by Fk506

In a first experiment, it was demonstrated that the signaling activity of pSELFFY bait constructs can be inhibited by the inhibitory prey pMET7-fPPD1-FKBP12, comprising the PTP-1B phosphatase domain. 400,000 HEK293T cells (six-well plate) were transfected with a combination of following plasmids:
1. pSELFFY-ALK4 (1 µg)+pMET7mcs (1 µg)+pXP2d2-rPAP1-luci (200 ng)+pUT651 (25 ng)
2. pSELFFY-ALK4 (1 µg)+pMET7-fPPD1-FKBP12 (500 ng)+pMET7mcs (500 ng)+pXP2d2-rPAP1-luci (200 ng)+pUT651 (25 ng)
3. pSELFFY-EpoR (1 µg)+pMET7mcs (1 µg)+pXP2d2-rPAP1-luci (200 ng)+pUT651 (25 ng)
4. pSELFFY-EpoR (1 µg)+pMET7-fPPD1-FKBP12 (500 ng)+pMET7mcs (500 ng)+pXP2d2-rPAP1-luci (200 ng)+pUT651 (25 ng)

pMET7mcs was added as indifferent plasmid to transfect each time with an equal amount of DNA.

Two days after transfection, cells were seeded in black well plates (approximately 10,000 cells/well) and treated or not with Epo (5 ng/ml). Twenty-four hours after stimulation, rPAP1 and constitutive reporter (pUT651) activity was assayed by measuring luciferase and beta-galactosidase activity, respectively.

Luciferase and beta-galactosidase activities were measured in triplicate. A representative experiment is shown in FIG. 5. The results are expressed as fold inhibition, when the inhibitor is recruited by the ALK4-FKBP12 interaction, compared to a situation where the inhibitor is present, but not recruited to the receptor via the bait.

To demonstrate that the ALK4-FKBP12 interaction inhibitor FK506 can restore the signaling by the pSELFFY-ALK4 bait, 400,000 HEK293T cells (six-well plate) were transfected with a combination of following plasmids:
1. pSELFFY-ALK4 (1 µg)+pMET7-fPPD1-FKBP12 (1 µg)+pXP2d2-rPAP1-luci (200 ng)+pUT651 (25 ng)
2. pSELFFY-ALK4 (1 µg)+pMET7-fPPD1-FKBP12 (500 ng)+pMET7mcs (500 ng)+pXP2d2-rPAP1-luci (200 ng)+pUT651 (25 ng)
3. pSELFFY-ALK4 (1 µg)+pMET7-fPPD1-FKBP12 (250 ng)+pMET7mcs (750 ng)+pXP2d2-rPAP1-luci (200 ng)+pUT651 (25 ng)
4. pSELFFY-EpoR (1 µg)+pMET7-fPPD1-FKBP12 (1 µg)+pXP2d2-rPAP1-luci (200 ng)+pUT651 (25 ng)
5. pSELFFY-EpoR (1 µg)+pMET7-fPPD1-FKBP12 (500 ng)+pMET7mcs (500 ng)+pXP2d2-rPAP1-luci (200 ng)+pUT651 (25 ng)
5. pSELFFY-EpoR (1 µg) pMET7-fPPD1-FKBP12 (250 ng)+pMET7mcs (750 ng)+pXP2d2-rPAP1-luci (200 ng)+pUT651 (25 ng)

pMET7mcs was added as indifferent plasmid, to transfect each time with an equal amount of DNA.

Two days after transfection, cells were seeded in black well plates (approximately 10,000 cells/well) and pretreated with various concentrations of FK506 as indicated. Epo was added after four hours to the treated cells (5 ng/ml). Twenty-four hours after stimulation, luciferase and beta-galactosidase activities were measured.

A representative experiment of triplicate luciferase measurements is shown in FIG. 6. The values have been normalized using background luciferase activities (fold induction) and by using an irrelevant bait construct (pSELFFY-EpoR, exp. 4-6) to correct for toxicity of FK506 on the cells. From these experiments, it is clear that the inhibition by the bait-prey interaction can be blocked, in a dose dependent manner, by addition of the inhibitor of the interaction.

TABLE 1 primers used for the constructions.

| MBU-O-302 | Forward mSOCS3 primer | 5' GAAGATCTGTGCGCCATGGTCACCCACAGCAAGTT (SEQ ID NO: 7 of the accompanying, and incorporated herein by this reference, SEQUENCE LISTING) |

TABLE 1-continued primers used for the constructions.

| | | |
|---|---|---|
| MBU-O-303 | Reverse mSOCS3 primer | 5' GCTCTAGATTTTGCTCCTTAAAGTGGAGCATCATA (SEQ ID NO: 8) |
| MBU-O-447 | Forward mLepR primer | 5' GCTTAATTAACGGGCTGTATGTCATTGTACC (SEQ ID NO: 12) |
| MBU-O-448 | Reverse mLepR primer | 5' CGTCTAGATTAGCGGCCGCTTACTAGTGAGCTCGTCGA CCCACCCACAGTTAAGTCACACATC (SEQ ID NO: 13) |
| MBU-O-837 | Forward mSOCS3 primer | 5' GCGAGATCTCAGAATTCGTCACCCACAGCAAGTTTCC (SEQ ID NO: 19) |
| MBU-O-1001 | mutagenesis BspEI CIS | 5' CTCCTACCTTCGGGAATCCGGATGGTACTGGGGTTC (SEQ ID NO: 20) |
| MBU-O-1002 | mutagenesis BspEI CIS | 5' GAACCCCAGTACCATCCGGATTCCCGAAGGTAGGAG (SEQ ID NO: 21) |
| MBU-O-1003 | mutagenesis XhoI CIS | 5' CAGCCCTTTGTGCGCCGCTCGAGTGCCCGCAGCTTAC (SEQ ID NO: 22) |
| MBU-O-1004 | mutagenesis XhoI CIS | 5' GTAAGCTGCGGGCACTCGAGCGGCGCACAAAGGGCTG (SEQ ID NO: 23) |
| MBU-O-1005 | mutagenesis BspEI SOCS3 | 5' CGCAAGCTGCAGGAGTCCGGATTCTACTGGAGTGCC (SEQ ID NO: 24) |
| MBU-O-1006 | mutagenesis BspEI SOCS3 | 5' GGCACTCCAGTAGAATCCGGACTCCTGCAGCTTGCG (SEQ ID NO: 25) |
| MBU-O-1007 | mutagenesis XhoI SOCS3 | 5' GAGCCGACCTCTCTCGAGCAACGTGGCTACCCTC (SEQ ID NO: 26) |
| MBU-O-1008 | mutagenesis XhoI SOCS3 | 5' GAGGGTAGCCACGTTGCTCGAGAGAGGTCGGCTC (SEQ ID NO: 27) |
| MBU-O-157 | Y985F mutagenesis in mLepR | F GAGACAACCCTCAGTTAAATTTGCAACTCTGGTCAGCAA CG (SEQ ID NO: 1) |
| MBU-O-158 | Y985F mutageneis in mLepR | R CGTTGCTGACCAGAGTTGCAAATTTAACTGAGGGTTGTC TC (SEQ ID NO: 2) |
| MBU-O-159 | Y1077F mutagenesis in mLepR | F GGGAGAAGTCTGTCTGTTTTCTAGGGGTCACCTCCGTCA AC (SEQ ID NO: 3) |
| MBU-O-160 | Y1077F mutagenesis in mLepR | R GTTGACGGAGGTGACCCCTAGAAAACAGACAGACTTCTC CC (SEQ ID NO: 4) |
| MBU-O-161 | Y1138F mutagenesis in mLepR | F CTGGTGAGAACTTTGTACCTTTTATGCCCCAATTTCAAA CCTG (SEQ ID NO: 5) |
| MBU-O-162 | Y1138F mutagenesis in mLepR | R CAGGTTTGAAATTGGGGCATAAAAGGTACAAAGTTCTCA CCAG (SEQ ID NO: 6) |
| MBU-O-443 | hgp130 primer | R GCGAATTCCGAACCGCCCTGAGGCATGTAGCCGCC (SEQ ID NO: 9) |
| MBU-O-445 | SV40 LargeT primer | F GCGAATTCGAAGCAGAGGAAACTAAACAAGTG (SEQ ID NO: 10) |
| MBU-O-446 | SV40 LargeT primer | R CGTCTAGAGCGGCCGCAGATCTCGAGTCGCGATTATGTT TCAGGTTCAGGGGGAG (SEQ ID NO: 11) |
| MBU-O-586 | hgp130 primer | F GACGGGCCGCCACCATGGATTACAAGGATGACGACGAT AAGATCTCGACCGTGGTACACAGTGGC (SEQ ID NO: 14) |
| MBU-O-675 | hEpoR intr. fragment primer | F GGCGAGCTCGGTGCTGGACAAATGGTTGC (SEQ ID NO: 15) |

TABLE 1-continued primers used for the constructions.

| | | |
|---|---|---|
| MBU-O-676 | hEpoR intr. fragment primer | R CGCTCTAGATTACTTTAGGTGGGGTGGGGTAG (SEQ ID NO: 16) |
| MBU-O-677 | mCIS primer | F GCGGAATTCGTCCTCTGCGTACAGGGATC (SEQ ID NO: 17) |
| MBU-O-678 | mCIS primer | R GCCTCTAGATCAGAGTTGGAAGGGGTACTG (SEQ ID NO: 18) |
| MBU-O-1250 | Forward FKBP12 full size | GCGAGATCTCTGAATTCGGAGTGCAGGTGGAAACCATC (SEQ ID NO: 28) |
| MBU-O-1251 | Reverse FKBP12 full size | CGCTCTAGATTATGCGGCCGCTTCCAGTTTTAGAAGCTCC (SEQ ID NO: 29) |
| MBU-O-1261 | Forward ALK4 cytoplasmic domain | GCGAGAGCTCAAACTATCACCAGCGTGTC (SEQ ID NO: 30) |
| MBU-O-1262 | Reverse ALK4 cytoplasmic domain | CGCTGCGGCCGCTTAAATCTTCACATCTTCCTGC (SEQ ID NO: 31) |
| MBU-O-1465 | Forward PTP-1B phosphatase domain | GCGGGATCCTTATGGAGATGGAAAAGGAG (SEQ ID NO: 32) |
| MBU-O-1466 | Reverse PTP-1B phosphatase domain | CGCTGAATTCACTTCCACCAGACCCACCAGAGCCTCCCTCG TGGGAAAGCTCCTTCC (SEQ ID NO: 33) |

REFERENCES

Chung C. D., J. Liao, B. Liu, X. Rao, P. Jay, P. Berta, and K. Shuai (1997). Specific inhibition of Stat3 signal transduction by PIAS3. *Science* 278:1803-1805.

Eyckerman S., W. Waelput, A. Verhee, D. Broekaert, J. Vandekerckhove, and J. Tavernier (1999). Analysis of Tyr to Phe and fa/fa leptin receptor mutations in the PC12 cell line. *Eur. Cytokine Netw.* 10:549-556.

Fields S. and O. K. Song (1989). A novel genetic system to detect protein-protein interactions. *Nature* 340:245-246.

Graham F. L. and A. J. van der Eb (1973). Transformation of rat cells by DNA of human adenovirus 5. *Virology* 54:536-539.

Grimm S. L. and S. K. Nordeen (1999). Luciferase reporter gene vectors that lack potential AP-1 sites. *Biotechniques* 27:220-222.

Pattyn E., X. Van Ostade, L. Schauvliege, A. Verhee, M. Kalai, J. Vandekerckhove, and J. Tavernier (1999). Dimerization of the interferon type I receptor IFNaR2-2 is sufficient for induction of interferon effector genes but not for full antiviral activity. *J. Biol. Chem.* 274:34838-34845.

Takebe Y., M. Seiki, J. Fujisawa, P. Hoy, K. Yokota, K. Arai, M. Yoshida, and N. Arai (1988). SR alpha promoter: an efficient and versatile mammalian cDNA expression system composed of the simian virus 40 early promoter and the R-U5 segment of human T-cell leukemia virus type 1 log terminal repeat. *Mol. Cell. Biol.* 8:466-472.

ten Dijke P., H. Ichijo, P. Franzen, P. Schulz, J. Saras, H. Toyoshima, C. H. Helding, and K. Miyazono (1993). Activin receptor-like kinases: a novel subclass of cell-surface receptors with predicted serine/threonine kinase activity. *Oncogene* 8:2879-2887.

Wang T., P. K. Donahoe and A. S. Zervos (1994). Specific interaction of type I receptors of the TGF-beta family with the immunophilin FKBP12. *Science* 256:674-676.

Wiley J. C., L. A. Wailes, R. L. Idzerda, and G. S. McKnight (1999). Role of regulatory subunits and protein kinase inhibitor (PKI) in determining nuclear localization and activity of the catalytic subunit of protein kinase A. *J. Biol. Chem.* 274:6381-6387.

What is claimed is:

1. A receptor complex comprising:
   a recombinant receptor polypeptide comprising an extracellular ligand-binding domain derived from a receptor, and a cytoplasmic domain comprising (a) a receptor-derived cytoplasmic domain comprising a JAK-binding site and at least one activation site that is a tyrosine residue and (b) a first interacting polypeptide, heterologous to the receptor-derived cytoplasmic domain, and
   a recombinant polypeptide comprising a second interacting polypeptide, interacting with the first interacting polypeptide, and an inhibitor of the activation site of the cytoplasmic domain of the recombinant receptor, wherein the inhibitor is selected from the group consisting of a member of the SOCS family, a JAK-phosphatase, and a STAT-phosphatase,
   wherein the receptor complex is activated by binding of a ligand to the ligand-binding domain and by disruption of the interaction between the first interacting polypeptide and the second interacting polypeptide.

2. The receptor complex of claim 1, wherein the recombinant receptor is a homomultimerizing receptor.

3. The receptor complex of claim 1, wherein the recombinant receptor is a heteromultimerizing receptor.

4. The receptor complex of claim 1, wherein the binding of the second interacting polypeptide is dependent upon the first interacting polypeptide's modification state.

5. The receptor complex of claim 4, wherein the modification state is presence or absence of phosphorylation, acetylation, acylation, methylation, ubiquitinilation or glycosylation.

6. The receptor complex of claim 4, wherein the modification state is dependent upon binding of a ligand to the ligand-binding domain.

7. The receptor complex of claim 2, wherein the binding of the second interacting polypeptide is dependent upon the first interacting polypeptide's modification state.

8. The receptor complex of claim 7, wherein the modification state is presence or absence of phosphorylation, acetylation, acylation, methylation, ubiquitinilation or glycosylation.

9. The receptor complex of claim 7, wherein the modification state is dependent upon binding of a ligand to the ligand-binding domain.

10. The receptor complex of claim 8, wherein the modification state is dependent upon binding of a ligand to the ligand-binding domain.

11. The receptor complex of claim 3, wherein the binding of the second interacting polypeptide is dependent upon the first interacting polypeptide's modification state.

12. The receptor complex of claim 11, wherein the modification state is presence or absence of phosphorylation, acetylation, acylation, methylation, ubiquitinilation or glycosylation.

13. The receptor complex of claim 11, wherein the modification state is dependent upon binding of a ligand to the ligand-binding domain.

14. The receptor complex of claim 12, wherein the modification state is dependent upon binding of a ligand to the ligand-binding domain.

* * * * *

SEQUENCE LISTING

<160> NUMBER OF SEQ ID NOS: 35

<210> SEQ ID NO 1
<211> LENGTH: 41
<212> TYPE: DNA
<213> ORGANISM: Artificial Sequence
<220> FEATURE:
<223> OTHER INFORMATION: Description of Artificial Sequence: forward primer; MBU-O-157; Y985F mutagenesis in mLepR

<400> SEQUENCE: 1
gagacaaccc tcagttaaat ttgcaactct ggtcagcaac g            41

```
<210> SEQ ID NO 2
<211> LENGTH: 41
<212> TYPE: DNA
<213> ORGANISM: Artificial Sequence
<220> FEATURE:
<223> OTHER INFORMATION: Description of Artificial Sequence: reverse
      primer; MBU-O-158; Y985F mutagenesis in mLepR

<400> SEQUENCE: 2
cgttgctgac cagagttgca aatttaactg agggttgtct c                         41

<210> SEQ ID NO 3
<211> LENGTH: 41
<212> TYPE: DNA
<213> ORGANISM: Artificial Sequence
<220> FEATURE:
<223> OTHER INFORMATION: Description of Artificial Sequence: forward
      primer; MBU-O-159; Y1077F mutagenesis in mLepR

<400> SEQUENCE: 3
gggagaagtc tgtctgtttt ctaggggtca cctccgtcaa c                         41

<210> SEQ ID NO 4
<211> LENGTH: 41
<212> TYPE: DNA
<213> ORGANISM: Artificial Sequence
<220> FEATURE:
<223> OTHER INFORMATION: Description of Artificial Sequence: reverse
      primer; MBU-O-160; Y1077F mutagenesis in mLepR

<400> SEQUENCE: 4
gttgacggag gtgaccccta gaaaacagac agacttctcc c                         41

<210> SEQ ID NO 5
<211> LENGTH: 43
<212> TYPE: DNA
<213> ORGANISM: Artificial Sequence
<220> FEATURE:
<223> OTHER INFORMATION: Description of Artificial Sequence: forward
      primer; MBU-O-161; Y1138F mutagenesis in mLepR

<400> SEQUENCE: 5
ctggtgagaa ctttgtacct tttatgcccc aatttcaaac ctg                       43

<210> SEQ ID NO 6
<211> LENGTH: 43
<212> TYPE: DNA
<213> ORGANISM: Artificial Sequence
<220> FEATURE:
<223> OTHER INFORMATION: Description of Artificial Sequence: reverse
      primer; MBU-O-162; Y1138F mutagenesis in mLepR

<400> SEQUENCE: 6
caggtttgaa attggggcat aaaaggtaca aagttctcac cag                       43

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence: forward
      primer; MBU-O-302; mSOCS3 primer

<400> SEQUENCE: 7
gaagatctgt gcgccatggt cacccacagc aagtt                                35
```

```
<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: reverse
      primer; MBU-O-303; mSOCS3 primer

<400> SEQUENCE: 8
gctctagatt ttgctcctta aagtggagca tcata                              35

<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence: reverse
      primer; MBU-O-443; hgp 130 primer

<400> SEQUENCE: 9
gcgaattccg aaccgccctg aggcatgtag ccgcc                              35

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence: forward
      pirmer; MBU-O-445; SV40 Large T primer

<400> SEQUENCE: 10
gcgaattcga agcagaggaa actaaacaag tg                                 32

<210> SEQ ID NO 11
<211> LENGTH: 55
<212> TYPE: DNA
<213> ORGANISM: Artificial Sequence
<220> FEATURE:
<223> OTHER INFORMATION: Description of Artificial Sequence: reverse
      primer; MBU-O-446; SV40 Large T primer

<400> SEQUENCE: 11
cgtctagagc ggccgcagat ctcgagtcgc gattatgttt caggttcagg gggag        55

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: forward
      primer; MBU-O-447; mLepR primer

<400> SEQUENCE: 12
gcttaattaa cgggctgtat gtcattgtac c                                  31

<210> SEQ ID NO 13
<211> LENGTH: 63
<212> TYPE: DNA
<213> ORGANISM: Artificial Sequence
<220> FEATURE:
<223> OTHER INFORMATION: Description of Artificial Sequence: reverse
      primer; MBU-O-448; mLepR primer

<400> SEQUENCE: 13
cgtctagatt agcggccgct tactagtgag ctcgtcgacc cacccacagt taagtcacac   60
atc                                                                 63
```

```
<210> SEQ ID NO 14
<211> LENGTH: 66
<212> TYPE: DNA
<213> ORGANISM: Artificial Sequence
<220> FEATURE:
<223> OTHER INFORMATION: Description of Artificial Sequence: forward
      primer; MBU-O-586; hgp 130 primer

<400> SEQUENCE: 14
gacgggcccg ccaccatgga ttacaaggat gacgacgata agatctcgac cgtggtacac      60
agtggc                                                                66

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence: forward
      primer; MBU-O-675; hEpoR intr. fragment primer

<400> SEQUENCE: 15
ggcgagctcg gtgctggaca aatggttgc                                       29

<210> SEQ ID NO 16
<211> LENGTH: 32
<212> TYPE: DNA
<213> ORGANISM: Artificial Sequence
<220> FEATURE:
<223> OTHER INFORMATION: Description of Artificial Sequence: reverse
      primer; MBU-O-676; hEpoR intr. fragment primer

<400> SEQUENCE: 16
cgctctagat tactttaggt ggggtggggt ag                                   32

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence: forward
      primer; MBU-O-677; mCIS primer

<400> SEQUENCE: 17
gcggaattcg tcctctgcgt acagggatc                                       29

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: reverse
      primer; MBU-O-678; mCIS primer

<400> SEQUENCE: 18
gcctctagat cagagttgga aggggtactg                                      30

<210> SEQ ID NO 19
<211> LENGTH: 37
<212> TYPE: DNA
<213> ORGANISM: Artificial Sequence
<220> FEATURE:
<223> OTHER INFORMATION: Description of Artificial Sequence: forward
      primer; MBU-O-837; mSOCS3 primer

<400> SEQUENCE: 19
gcgagatctc agaattcgtc acccacagca agtttcc                              37
```

```
<210> SEQ ID NO 20
<211> LENGTH: 36
<212> TYPE: DNA
<213> ORGANISM: Artificial Sequence
<220> FEATURE:
<223> OTHER INFORMATION: Description of Artificial Sequence: primer;
      MBU-O-1001; mutagenesis BspEI CIS

<400> SEQUENCE: 20
ctcctacctt cgggaatccg gatggtactg gggttc                                 36

<210> SEQ ID NO 21
<211> LENGTH: 36
<212> TYPE: DNA
<213> ORGANISM: Artificial Sequence
<220> FEATURE:
<223> OTHER INFORMATION: Description of Artificial Sequence: primer;
      MBU-O-1002; mutagenesis BspEI CIS

<400> SEQUENCE: 21 gaacccagt accatccgga ttcccgaagg taggag                                  36

<210> SEQ ID NO 22
<211> LENGTH: 37
<212> TYPE: DNA
<213> ORGANISM: Artificial Sequence
<220> FEATURE:
<223> OTHER INFORMATION: Description of Artificial Sequence: primer;
      MBU-O-1003; mutagenesis XhoI CIS

<400> SEQUENCE: 22 cagcccttg tgcgccgctc gagtgcccgc agcttac                                 37

<210> SEQ ID NO 23
<211> LENGTH: 37
<212> TYPE: DNA
<213> ORGANISM: Artificial Sequence
<220> FEATURE:
<223> OTHER INFORMATION: Description of Artificial Sequence: primer;
      MBU-O-1004; mutagenesis XhoI CIS

<400> SEQUENCE: 23
gtaagctgcg ggcactcgag cggcgcacaa agggctg                                37

<210> SEQ ID NO 24
<211> LENGTH: 36
<212> TYPE: DNA
<213> ORGANISM: Artificial Sequence
<220> FEATURE:
<223> OTHER INFORMATION: Description of Artificial Sequence: primer;
      MBU-O-1005; mutagenesis BspEI SOCS3

<400> SEQUENCE: 24
cgcaagctgc aggagtccgg attctactgg agtgcc                                 36

<210> SEQ ID NO 25
<211> LENGTH: 36
<212> TYPE: DNA
<213> ORGANISM: Artificial Sequence
<220> FEATURE:
<223> OTHER INFORMATION: Description of Artificial Sequence: primer;
      MBU-O-1006; mutagenesis BspEI SOCS3

<400> SEQUENCE: 25
ggcactccag tagaatccgg actcctgcag cttgcg                                 36
```

```
<210> SEQ ID NO 26
<211> LENGTH: 34
<212> TYPE: DNA
<213> ORGANISM: Artificial Sequence
<220> FEATURE:
<223> OTHER INFORMATION: Description of Artificial Sequence: primer;
      MBU-O-1007; mutagenesis XhoI SOCS3

<400> SEQUENCE: 26
gagccgacct ctctcgagca acgtggctac cctc                                34

<210> SEQ ID NO 27
<211> LENGTH: 34
<212> TYPE: DNA
<213> ORGANISM: Artificial Sequence
<220> FEATURE:
<223> OTHER INFORMATION: Description of Artificial Sequence: primer;
      MBU-O-1008; mutagenesis XhoI SOCS3

<400> SEQUENCE: 27
gagggtagcc acgttgctcg agagaggtcg gctc                                34

<210> SEQ ID NO 28
<211> LENGTH: 38
<212> TYPE: DNA
<213> ORGANISM: Artificial Sequence
<220> FEATURE:
<223> OTHER INFORMATION: Description of Artificial Sequence: MBU-O-1250,
      forward primer FKBP12 full size

<400> SEQUENCE: 28
gcgagatctc tgaattcgga gtgcaggtgg aaaccatc                            38

<210> SEQ ID NO 29
<211> LENGTH: 40
<212> TYPE: DNA
<213> ORGANISM: Artificial Sequence
<220> FEATURE:
<223> OTHER INFORMATION: Description of Artificial Sequence: MBU-O-1251,
      reverse primer FKBP12 full size

<400> SEQUENCE: 29
cgctctagat tatgcggccg cttccagttt tagaagctcc                          40

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence: MBU-O-1261,
      forward primer ALK4 cytoplasmic domain

<400> SEQUENCE: 30
gcgagagctc aaactatcac cagcgtgtc                                      29

<210> SEQ ID NO 31
<211> LENGTH: 34
<212> TYPE: DNA
<213> ORGANISM: Artificial Sequence
<220> FEATURE:
<223> OTHER INFORMATION: Description of Artificial Sequence: MBU-O-1262,
      reverse primer ALK4 cytoplasmic domain

<400> SEQUENCE: 31
cgctgcggcc gcttaaatct tcacatcttc ctgc                                34
```

```
<210> SEQ ID NO 32
<211> LENGTH: 29
<212> TYPE: DNA
<213> ORGANISM: Artificial Sequence
<220> FEATURE:
<223> OTHER INFORMATION: Description of Artificial Sequence: MBU-O-1465,
      forward primer PTP-1B phosphatase domain

<400> SEQUENCE: 32
gcgggatcct tatggagatg gaaaaggag                                    29

<210> SEQ ID NO 33
<211> LENGTH: 57
<212> TYPE: DNA
<213> ORGANISM: Artificial Sequence
<220> FEATURE:
<223> OTHER INFORMATION: Description of Artificial Sequence: MBU-O-1466,
      reverse primer PTP-1B phosphatase domai

<400> SEQUENCE: 33
cgctgaattc acttccacca gacccaccag agcctccctc gtgggaaagc tccttcc     57

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: flag-tag
      sequence

<400> SEQUENCE: 34

Met Asp Tyr Lys Asp Asp Asp Lys Ile
                5                   10

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: FLAG tag
      sequence

<400> SEQUENCE: 35

Met Asp Tyr Lys Asp Asp Asp Asp Lys
                5
```